United States Patent [19]

Murakami et al.

[11] Patent Number: 5,091,474

[45] Date of Patent: Feb. 25, 1992

[54] EPOXY RESIN CURING AGENT BASED ON BLENDS CONTAINING DISECONDARY AROMATIC DIAMINES

[75] Inventors: Shinkichi Murakami; Osamu Watanabe, both of Iruma; Sadahisa Wada, Kamifukuoka; Makoto Miyazaki, Sakato; Hiroshi Inoue, Iruma, all of Japan

[73] Assignee: Toa Nenryo Kogyo Kabushiki Kaisha, Japan

[21] Appl. No.: 642,545

[22] Filed: Jan. 18, 1991

Related U.S. Application Data

[63] Continuation of Ser. No. 310,657, Feb. 15, 1989, abandoned.

[30] Foreign Application Priority Data

Feb. 17, 1988 [JP] Japan ................................. 63-34803
Apr. 29, 1988 [JP] Japan ................................ 63-108860

[51] Int. Cl.$^5$ ..................... C08G 59/56; C08G 59/50
[52] U.S. Cl. ............................ 525/109; 525/481; 525/486; 525/504; 528/27; 528/99; 528/104; 528/108; 528/109; 528/113; 528/120; 528/123; 528/124; 528/220; 528/228; 528/229; 528/332; 528/341; 528/407; 252/182.13
[58] Field of Search ............... 525/109, 481, 486, 504; 528/27, 104, 108, 109, 113, 120, 123, 124, 99, 220, 228, 229, 341, 332, 407; 252/182.13

[56] References Cited

U.S. PATENT DOCUMENTS

| | | | |
|---|---|---|---|
| 2,853,467 | 9/1958 | Bloom et al. ..................... | 528/120 |
| 2,899,407 | 8/1959 | Cyba .................................. | 528/104 |
| 2,981,711 | 8/1961 | Meyer et al. ..................... | 528/109 |
| 3,265,662 | 8/1966 | Kirwan et al. ................... | 528/124 |
| 3,359,216 | 12/1967 | Szobel et al. .................... | 528/124 |
| 3,397,177 | 8/1968 | Stolton ............................ | 528/104 |
| 3,595,833 | 7/1971 | Stolton ............................ | 528/124 |
| 3,634,275 | 1/1972 | Sundholm ....................... | 528/124 |
| 3,714,120 | 1/1973 | Labana et al. .................. | 528/124 |
| 3,755,253 | 8/1973 | Rice ................................. | 528/109 |
| 4,089,901 | 5/1978 | Ziemek et al. .................. | 260/570 |

FOREIGN PATENT DOCUMENTS 0159482 10/1985 European Pat. Off. .
0189048 7/1986 European Pat. Off. .
2308014 8/1974 Fed. Rep. of Germany .
61-40318 2/1986 Japan .
63-37117 2/1988 Japan .

OTHER PUBLICATIONS

Patent Abstracts of Japan, vol. 9, No. 74, Apr. 3, 1985, JP-A-59 207 920.
Patent Abstracts of Japan, vol. 10, No. 373, Dec. 1986, JP-A-61 166 828.

*Primary Examiner*—John Kight, III
*Assistant Examiner*—Frederick Krass
*Attorney, Agent, or Firm*—Lorusso & Loud

[57] ABSTRACT

A two component-type curing agent composition is disclosed which comprises a first curing agent which is capable of cross-linking an epoxy resin and which is at least one member selected from primary amines, phenolic compounds and acid anhydrides, and a second curing agent which is at least one compounds represented by the following general formula:

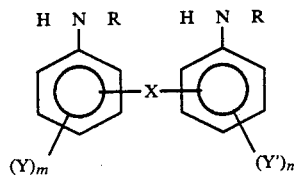

wherein X is $-CR_1R_2-$, $-CO-$, $-COO-$, $-SO_2-$, $-SO-$, $-S-$, $-O-$, $-NR_1-$, $-SiR_1R_2-$ or $-POR_1-$ where $R_1$ and $R_2$ each stands for hydrogen, a lower alkyl or a phenyl; Y and Y' each stands for hydrogen, a lower alkyl or an electron attracting group; R is a lower alkyl; and m and n each is an integer of 1–4.

6 Claims, 1 Drawing Sheet

EPOXY RESIN CURING AGENT BASED ON BLENDS CONTAINING DISECONDARY AROMATIC DIAMINES

This application is a continuation of application Ser. No. 07/310,657, filed Feb. 15, 1989, now abandoned.

This invention relates generally to a curing agent for epoxy resins and, more specifically, to a curing agent composition capable of providing an epoxy resin cured product having good modulus, hardness, heat resistance and toughness.

An aromatic diamine curing agent is known to provide an epoxy resin cured product having good chemical and physical properties such as modulus, hardness, and resistance to heat and chemicals. Representative of such diamine curing agents are m-phenylenediamine, diaminodiphenyl methane and diaminodiphenyl sulfone. These conventional curing agents, however, fail to give a cured product having good impact strength, anti-cracking strength, toughness, adhesivity and the like properties so that they are not suited for application to FRP (fiber reinforced plastics) matrix materials.

Accordingly, a flexibility-improving agent such as a monoepoxide, a diepoxide, a polythiol, a polyol, a polycarboxyl compound, an urethane prepolymer, a block rethane prepolymer, a polyamidoamine or the like is generally used for improving mechanical properties of the cured epoxy resin. Whilst the flexibility of the cured product can be improved to some extent by addition of such a flexibility-improving agent, the degree of improvement is still insufficient. Further, such a flexibility-improving agent tends to adversely affect the heat resistance, resistance to chemicals, weatherability, and mechanical strengths, such as modulus and hardness, of the cured product. Japanese Laid-Open Patent Application (Tokkyo Kokai) No. 61-40,318 discloses an epoxy resin curing agent having the following general formula:

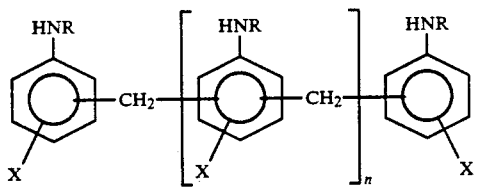

wherein R is the same or different and stands for hydrogen or an alkyl having 1-3 carbon atoms (where the hydrogen for the symbol R is 50 mole % or less based on the total moles of R); X stands for hydrogen, an alkyl having 1-3 carbons and an electron attractive group; and n is an integer of 1-5.

Since this curing agent contains 3-7 aniline moieties connected to each other through methylene linkages, a cured epoxy resin product obtained using same hardly contains straight molecular chains but has a high degree of cross-linkages. Thus, this curing agent fails to provide a high degree of toughness and flexibility. Furthermore, it has been found that the mechanical properties such as modulus, impact strength and hardness of the cured product are comparable to those of cured products obtained using conventional curing agents.

In accordance with the present invention, there is provided a curing agent composition comprising a first curing agent which is capable of cross-linking an epoxy resin and which is at least one member selected form primary amines, phenolic compounds and acid anhydrides, and a second curing agent which is at least one compounds represented by the following general formula (I):

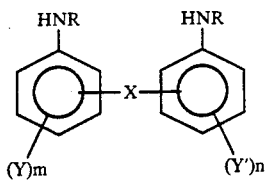

wherein X is $-CR_1R_2-$, $-CO-$, $-COO-$, $-SO_2-$, $-SO-$, $-S-$, $-O-$, $-NR_1-$, $-SiR_1R_2-$ or $-POR_1-$ where $R_1$ and $R_2$ each stands for hydrogen, a lower alkyl or a phenyl; Y and Y' each stands for hydrogen, a lower alkyl or an electron attracting group; R is a lower alkyl; and m and n each is an integer of 1-4.

In another aspect, the present invention provides a thermocurable composition comprising an epoxy resin; and the above curing agent composition.

The present inventors have found that the compound of the formula (I) can give a cured epoxy resin product having an improved toughness when used as an epoxy resin curing agent. However, the rigidity and mechanical strength of the cured product has been found not to be fully satisfactory. Upon further studies, it has now been found that when the compound of the formula (I) is used in conjuction with a conventional epoxy resin curing agent, i.e. first curing agent, the resulting cured product exhibits such excellent toughness, heat resistance, rigidity, mechanical strengths and other properties that are not expected from the use of them separately.

Such a synergetic effect is considered to result from a unique structure of the cured product. That is, when an epoxy resin is reacted with the mixed-type curing agent at an elevated temperature, there are formed, at an early stage of the curing, high molecular weight, linear polymers as a result of the reaction of the epoxy resin and the second curing agent having two secondary amino groups, which is considered to contribute to improvement in toughness of the resulting cured product. The hydroxyl groups of the linear polymers thus formed further react, at a later stage of the curing, with the glycidyl groups of the epoxy resin. At the same time, the first curing agent reacts with the epoxy resin. These two cross-linking reactions are considered to contribute to improvement in regidity and mechanical strengths of the cured product. Thus, the curing involves at least the above three types of cross-linking reactions which proceed homogeneously and continuously to give the cured product having complicated cross-linkages and uniform morphology.

BRIEF DESCRIPTION OF THE DRAWINGS

The present invention will now be described in detail below with reference to the accompanying drawings, in which.

Figure 1:
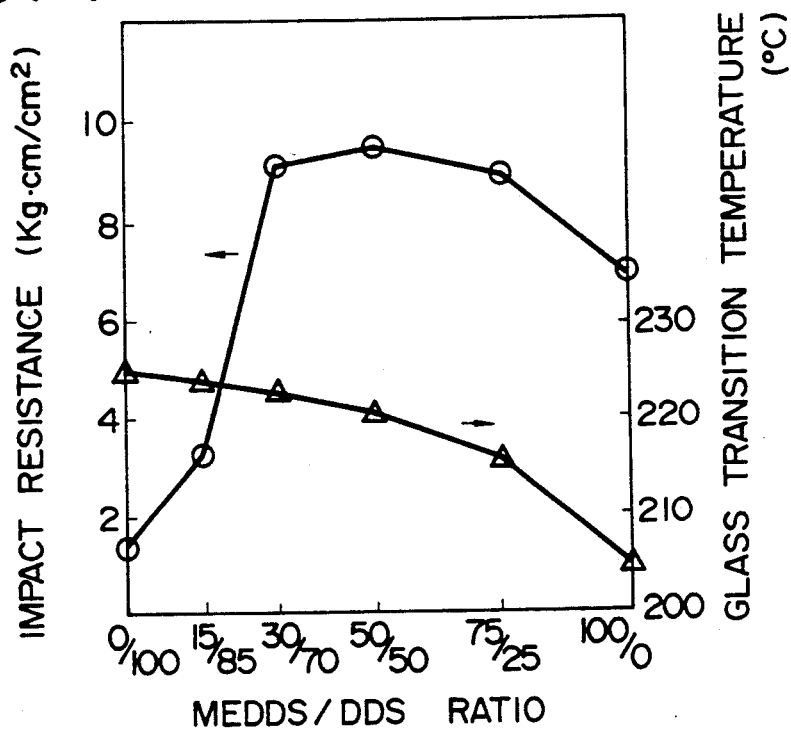
FIG. 1 is a graph showing the relationship between ratios of DDS to DMDDS and Izod strength and glass transition temperature Tg.

The epoxy resin curing agent composition according to the present invention includes the following first and second curing agents:

FIRST CURING AGENT

Primary amines such as aliphatic amines, aromatic amines, polyamidoamines and dicyanopolyamides; phenolic compounds such as bisphenols, phenolic resins, vinylphenol polymers; acid anhydrides such as maleic anhydride, succinic anhydride, methyltetrahydrophthalic anhydride, methylnadic anhydride and methylhexahydrophthalic anhydride; and mixtures thereof. Especially preferred curing agents are diaminodiphenylsulfone, diaminodiphenylmethane, dicyanodiamide and methylhexahydrophthalic anhydride.

SECOND CURING AGENT

Compounds of the general formula (I):

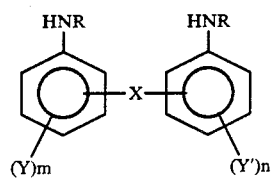

(I)

wherein X is —CR$_1$R$_2$—, —CO—, —COO—, —SO$_2$—, —SO—, —S—, —O—, —NR$_1$—, —SiR$_1$R$_2$— or —POR$_1$— where R$_1$ and R$_2$ each stands for hydrogen, a lower alkyl or a phenyl; Y and Y' each stands for hydrogen, a lower alkyl or an electron attracting group; R is a lower alkyl; and m and n each is an integer of 1-4.

Preferably, in the above formula (I), R is an alkyl having 1-3 carbon atoms, X is —CH$_2$—, —SO$_2$—, —CO—, —O—, —C(CH$_3$)$_2$— or —CHC$_6$H$_5$, Y and Y' each is hydrogen, a lower alkyl, a halogen, a nitro group or trifluoromethyl, R$_1$ and R$_2$ each is an alkyl having 1-3 carbon atoms, and m and n each is 1 or 2. Illustrative of suitable compounds of the formula (I) are as follows:

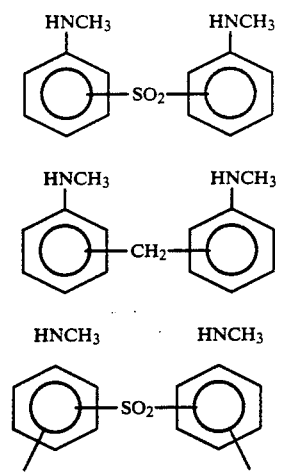

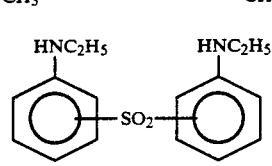

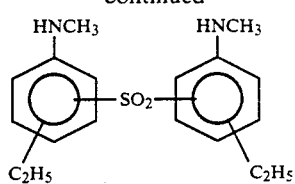

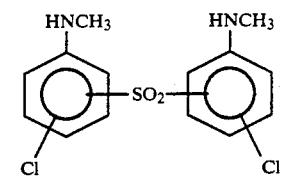

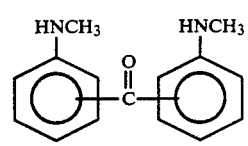

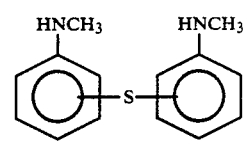

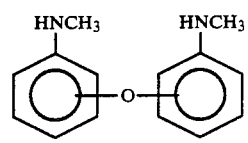

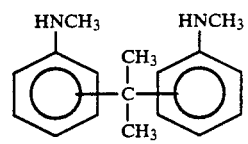

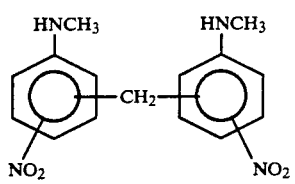

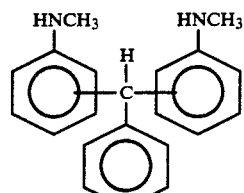

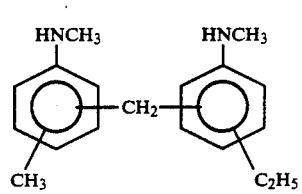

-continued

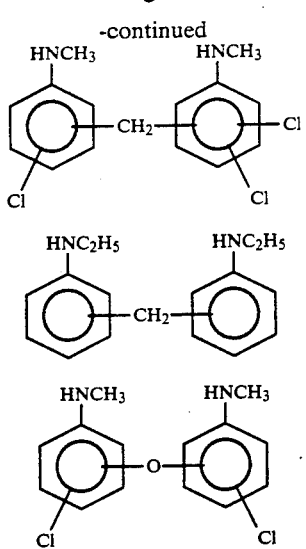

The proportion of the first curing agent to the second curing agent may be arbitrary. Preferably, the first and second curing agents are used in amounts so that said first and second curing agents account for 85 to 5% and 15 to 95%, respectively, more preferably 75 to 25% and 25 to 75%, respectively, of a total of the amounts of active hydrogen of the first and second curing agents.

The curing agent composition according to the present invention is effective to curing of any known epoxy resins. Examples of the epoxy resins include (1) glycidyl ether epoxy resins such as bisphenol A epoxy resins, bisphenol F epoxy resins, bisphenol S epoxy resins, novolak epoxy resins and brominated bisphenol epoxy resins; (2) cyclic aliphatic epoxy resins; (3) glycidyl ester epoxy resins, (4) glycidyl amine epoxy resins; and (5) heterocylic epoxy resins. Above all, the use of bisphenol A epoxy resins, bisphenol F epoxy resins, bisphenol S epoxy resins and glycidyl amine epoxy resins is especially preferred.

The curing agent composition is preferably used in an amount providing a ratio of equivalents of the active hydrogen of the curing agent composition per equivalent of the epoxy group of the epoxy resin of in the range of 0.6-1.4, more preferably 0.8-1.2.

The curing agent composition may be mixed as is or in the form of a solution in a solvent with the epoxy resin. The solvent may be, for example, a ketone such as acetone, methyl ethyl ketone or methyl isobutyl ketone; a cellosolve such as methyl cellosolve or ethyl cellosolve; an amide such as dimethyl formamide. The mixing may be performed at room temperature or, to facilitate homogeneous mixing, at elevated temperatures.

If desired, one or more additives may be incorporated into the resin mixtures. Illustrative of such additives are a reactive diluent such as olefin oxide, glycidyl methacrylate, styrene oxide or phenylglycidyl ether, a curing accelerator such as phenol, a tertiary amine, imidazole, a boron trifluoride complex salt, pyrazole or aminotriazole, and a filler such as silica powder, alumina powder, mica or calcium carbonate. Amounts of these additives may generally range up to 15% by weight for the reactive diluent, up to 5% by weight for the curing accelerator, and up to 70% by weight for the filler based on the total weight of the epoxy resin and the curing agent composition.

The curing is generally performed at temperatures of 100°-140° C. for 1-3 hours. This may be followed, if desired, by a post curing treatment which may be performed at 150°-220° C. for 1-3 hours.

The curing agent composition according to the present invention can provide a matrix resin, for example, for civil engineering and construction materials, coatings, lining materials, adhesives, molded materials, for electrical appliances (for example, mechanical parts, jigs and tools), fiber reinforced plastic composite materials and the like. The cured, epoxy resin articles obtained using the curing agent composition of the present invention has excellent heat resistance, modulus, hardness, chemical resistance, toughness, flexibility, rigidity, strength, anti-cracking property, impact strength and rupture strength. It is especially suited as an FRP matrix resin for the production of composite articles with high mechanical strength.

The following examples will further illustrate the present invention.

PREPARATION EXAMPLE 1

In 276 g (1 mole) of diaminodiphenylsulfone (DDS) in 1000 ml of a mixed solvent of water/ethanol (50/50) was charged 284 g (2 moles) of methyl iodide ($CH_3I$), and the mixture was reacted at 60° C. for 2 hours. The resulting crude product was purified by recrystallization with a water/ethanol (50/50) mixed solvent in duplicate.

The resulting product is identified by infrared absorption spectrum (IR) and gel permeation chromatography (GPC) and confirmed to be a pure product of an epoxy resin curing agent (B), the objective product according to the present invention, represented by the following formula:

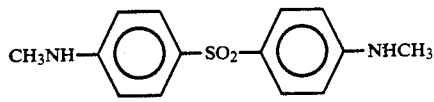

PREPARATION EXAMPLE 2

In 198 g (1 mole) of diaminodiphenylmethane (DDM) in 1000 ml of a mixed solvent of water/ethanol (50/50) was charged 284 g (2 moles) of methyl iodide ($CH_3I$), and the mixture was reacted at 60° C. for 2 hours. The resulting crude product was purified by recrystallization with a water/ethanol (50/50) mixed solvent in duplicate.

The resulting product is identified by IR and GPC and confirmed as a pure product of an epoxy resin curing agent (B), the objective product according to the present invention, represented by the following formula:

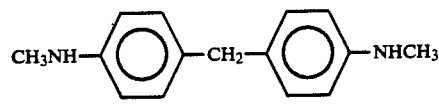

PREPARATION EXAMPLES 3-5

In place of diaminodiphenyl sulfone (DDS) used in Preparation Example 1, the process of Preparation Example 1 was followed in the same manner with the exception to use compounds of the following general formula:

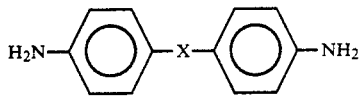

(in which X is —CO—, —S— or —C(CH₃)₂—), yielding the following compounds:

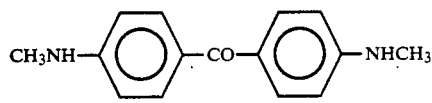

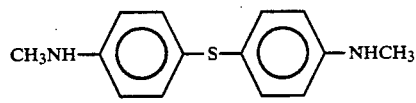

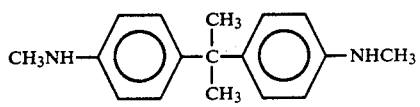

PREPARATION EXAMPLE 6

In place of diaminodiphenylsulfone (DDS) used in Preparation Example 1, the process of Preparation Example 1 was followed in the same manner with the exception to use a compound of the following general formula:

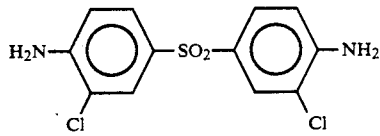

yielding a compound of the formula:

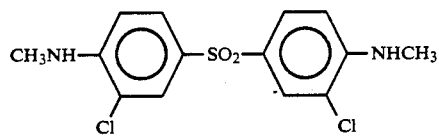

PREPARATION EXAMPLE 7

In a solution of 198 g (1 mole) of N,N-diaminodiphenyl-methane (DDM) in 1,000 ml of a water/ethanol (50/50) mixed solvent was charged 312 g (2 moles) of ethyl iodide (C₂H₅I), and the mixture was reacted at 60° C. for 3 hours. The resulting crude product was recrystallized twice from a water/ethanol (50/50) mixed solvent.

The resulting reaction product was identified by means of IR and GPC to have the following formula:

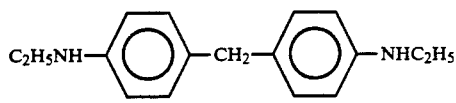

PREPARATION EXAMPLE 8

In place of diaminodiphenylsulfone (DDS) used in Preparation Example 1, the process of Preparation Example 1 was followed in the same manner with the exception to use a compound of the following general formula:

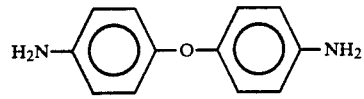

yielding a compound of the formula:

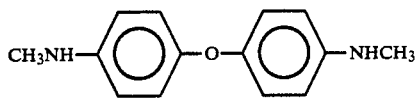

The mixed type curing agent according to the present invention will be described more in detail by way of examples.

EXAMPLES 1–3

Diaminodiphenylsulfone (DDS) as an epoxy resin curing agent (A) was mixed with the compound prepared in Preparation Example 1, (the epoxy resin curing agent (B)), to give mixed type epoxy resin curing agents having ratios of the agent (A) to the agnet (B), in terms of the amount of active hydrogen, of 25: 75 (Example 1), 50:50 (Example 2), and 70:30 (Example 3). Each of the mixed type epoxy resin curing agents was mixed stoichiometrically with an epoxy resin (Trade name: Epicoat 828; manufactured by Yuka Shell Epoxy K.K.), and the mixture was heated at about 70° C.

The resulting composition was then poured into a mold composed of two glass plates spaced apart from each other by a Teflon spacer, heated at 100° C. for 2 hours, and then cured at 200° C. for 2 hours in an oven. The cured product was then sliced into test pieces with a size of 30 cm ×30 cm and a thickness of 2 mm from a resin cast plate and the test pieces were subjected to various tests. Test results are shown in Table 1 below.

A prepreg was prepared by impregnating the above composition in carbon fiber (strength: 350 kg/mm²; modulus of elasticity: 32 t/mm²) arranged in the same direction. The prepreg was laminated in 12 layers and the resulting laminate was cured under the above curing conditions to give cured product which in turn was tested for compression after impact (CAI). This test result is also shown in Table 1 below.

EXAMPLES 4–6

Diaminodiphenylmethane (DDM) as the epoxy resin curing agent (A) was mixed with the epoxy resin curing agent (B) prepared in Preparation Example 2 to give mixed type epoxy resin curing agents having ratios of the agent (A) to the agent (B) in the active hydrogen amount of 25:75 (Example 4), 50:50 (Example 5), and 70:30 (Example 6). The mixed type epoxy resin curing agent was then mixed stoichiometrically with an epoxy resin (Trade name: Epicoat 828; manufactured by Yuka Shell Epoxy K.K.), and the mixture was heated at about 70° C.

Cured products and the prepregs were produced in the same manner as in Example 1 and were subjected to various tests, and test results are shown in Table 1 below.

EXAMPLES 7 and 8

Dicyanodiamide (DICY) as the epoxy resin curing agent (A) was mixed with the epoxy resin curing agents (B) prepared in Preparation Examples 1 and 2 to give mixed type epoxy resin curing agents in the ratio of the agent (A) to the agent (B) in the active hydrogen amount of 70 to 30 (Examples 7 and 8). Each of the mixed type epoxy resin curing agents was mixed stoichiometrically with an epoxy resin (Trade name: Epicoat 828; manufactured by Yuka Shell Epoxy K. K.), and the mixture was heated at about 70° C.

Cured products and the prepregs were prepared in the same manner as in Example 1 and were subjected to various tests and test results are shown in Table 1 below.

EXAMPLE 9

Methylhexahydrophthalic anhydride as the epoxy resin curing agent (A) was mixed with the epoxy resin curing agent (B) prepared in Preparation Example 1, to give a mixed type epoxy resin curing agent in the ratio of the former to the latter in the active hydrogen amount of 70:30. The mixed type epoxy resin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLE 10

Dicyanediamide (DICY) as the epoxy resin curing agent (A) was mixed with the epoxy resin curing agent (B) prepared in Preparation Example 7, to give a mixed type epoxy resin curing agent in the ratio of the former to the latter in the active hydrogen amount of 70:30. The mixed type epoxy resin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLE 11

Dicyanodiamide (DICY) and a curing agent represented by the following formula:

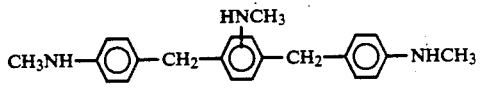

as the epoxy resin curing agent (A), were mixed with the epoxy resin curing agent (B) prepared in Preparation Example 2 to give a mixed type epoxy resin curing agent in the ratio of dicyane diamine (DICY) to the curing agent of the above formula to the curing agent (B) in the active hydrogen amount of 50:20:30. The mixed type epoxy resin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLES 12-15

Dicyanodiamide (DICY), as the epoxy resin curing agent (A), was mixed with the epoxy resin curing agent (B) prepared in Preparation Examples 3, 4, 5, and 6 to give mixed type epoxy resin curing agents in the ratio of the agent (A) to the agent (B) in the active hydrogen amount of 70:30. The mixed type epoxy resin curing agent was then mixed stoichiometrically with an epoxy resin (Trade name: Epicoat 828; manufacturer: Yuka Shell Epoxy K.K.), and the mixture was heated at about 70° C.

The cured product and the prepreg produced in the same manner as in Example 1 were subjected to various tests, and test results are shown in Table 1 below.

EXAMPLE 16

Diaminodiphenylsulfone (DDS) and dicyanodiamide (DICY), as the epoxy resin curing agent (A), were mixed with the epoxy resin curing agent (B) prepared in Preparation Example 1 to give a mixed type epoxy resin curing agent in the ratio of diaminodiphenylsulfone (DDS) to dicyanodiamide (DCY) to the curing agent (B) in the active hydrogen amount of 35:35:30. The mixed type epoxy resin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLE 17

Phenol novolak (manufactured by Gunei Kagaku Kogyo K.K.), as the epoxy resin curing agent (A), were mixed with the epoxy resin curing agent (B) prepared in Preparation Example 1 to give a mixed type epoxy resin curing agent in the ratio of the former to the latter of 70:30 in the active hydrogen amount. The mixed typ e epoxy resin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLE 18

Dicyanodiamide (DICY), as the epoxy resin curing agent (A), were mixed with the epoxy resin curing agent (B) prepared in Preparation Example 8 to give a mixed type epoxy resin curing agent in the ratio of the former to the latter of 70:30 in the active hydrogen amount. The mixed type epoxyresin curing agent was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

REFERENCE EXAMPLE 1

As an epoxy resin curing agent, only the epoxy resin curing agent (B) prepared in Preparation Example 1 was mixed stoichiometrically with an epoxy resin (Trade name: Epicoat 828; manufacturer: Yuka Shell Epoxy K.K.), and the mixture was heated at about 70° C.

The cured product and the prepreg prepared in the same manner as in Example 1 were subjected to various tests, and test results are shown in Table 1 below.

COMPARATIVE EXAMPLE 1

DDS used conventionally as an epoxy resin curing agent was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

EXAMPLE 19

DDS, as the epoxy resin curing agent (A), was mixed with the epoxy resin curing agent (B) prepared in Preparation Example 1 to give a mixed type epoxy resin curing agent in the ratio of the former to the latter in the active hydrogen amount of 85:15, and the mixture was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

REFERENCE EXAMPLE 2

As an epoxy resin curing agent, only the epoxy resin (B) prepared in Preparation Example 2 was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

COMPARATIVE EXAMPLE 2

DDM used conventionally as an epoxy resin curing agent was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

REFERENCE EXAMPLE 20

DDM used conventionally as the epoxy resin curing agent (A), was mixed with the epoxy resin curing agent (B) prepared in Preparation Example 2 to give a mixed type epoxy resin curing agent in the ratio of the former to the latter in the active hydrogen amount of 85:15, and the mixture was then mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

COMPARATIVE EXAMPLE 3

DICY used conventionally as an epoxy resin curing agent was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

COMPARATIVE EXAMPLE 4

Methylhexahydrophthalic anhydride used conventionally as an epoxy resin curing agent was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

COMPARATIVE EXAMPLE 5

Phenol novolak (Gunei Kagaku Kogyo K.K.) used conventionally as an epoxy resin curing agent was mixed stoichiometrically with an epoxy resin (Trade name: Epicoat 828; manufactured by Yuka Shell Epoxy K.K.), and the mixture was heated at about 70° C.

The cured product and the prepreg prepared in the same manner as in Example 1 were subjected to various tests, and test results are shown in Table 1 below.

From the test results shown in Table 1, it is to be understood that the mixed type epoxy resin curing agents according to the present invention have remarkably improved properties in terms of rigidity and hardness, particularly in terms of toughness, and furthermore improve mechanical strength when used particularly for FRP, as compared with conventional agents.

Figure 2:
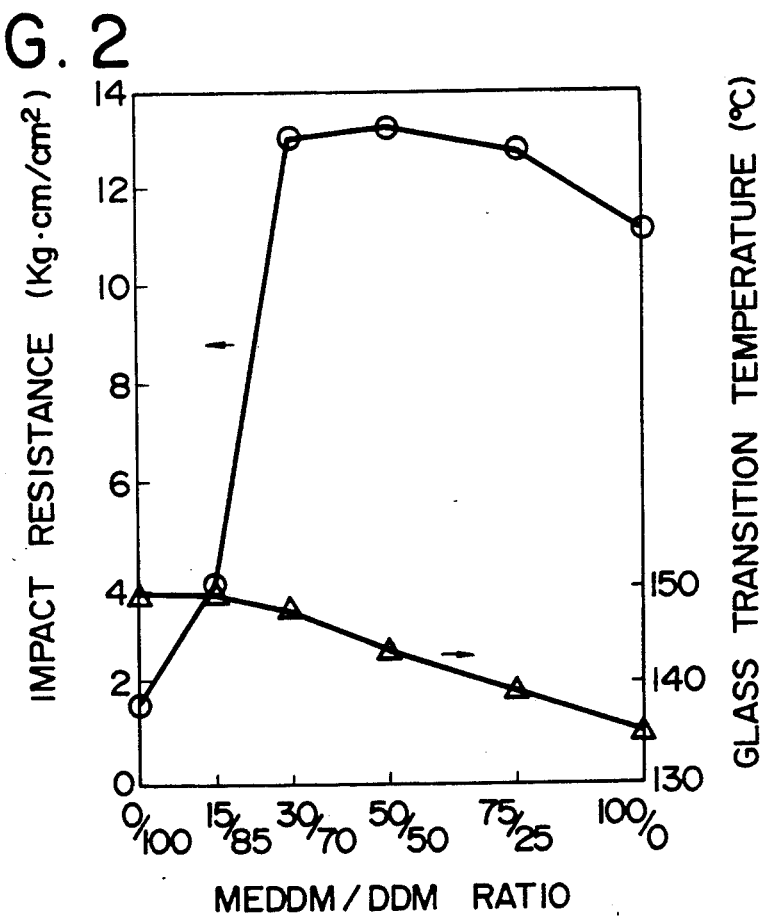
FIG. 2 is a graph, similar to FIG. 1, showing the relationship between ratios of DDM to DMDDM and Izod strength and Tg.

The test results of Examples 1-6, Reference Examples 1-4 and Comparative Example 1 and 2 are also shown by way of graphs in FIGS. 1 and 2.

FIG. 1 show relationships of impact resistance (IZOD) and glass transiton temperature (Tg) with proportion of curing agents (A) and (B) of a mixed type curing agent compositon in the case where diaminodiphenyl sulfone (DDS) as an epoxy resin curing agent (A) is mixed with dimethyldiaminodiphenylsulfone (DMDDS) as an epoxy resin curing agent (B). FIG. 2 shows relationships of impact resistance (IZOD) and glass transition temperature (Tg) with proportion of the curing agent in the case where diaminodiphenylmethane (DDM) as an epoxy resin curing agent (A) is mixed with dimethyldiaminodiphenylmethane (DMDDM) as an epoxy resin curing agent (B).

It will be understood from FIGS. 1 and 2 that an IZOD value in the case of the present invention becomes considerably larger than those expected from a mere sum. In particular, when the epoxy resin curing agent (B) is mixed in the proportion of 15% or more in terms of the active hydrogen amount, the IZOD value is significantly improved. It is further to be noted that when the epoxy resin curing agent (B) is mixed in the proportion of 50% in terms of active hydrogen amount, the IZOD value reaches the maximum value. It is thus assumed that the growth of linear polymers and the formation of cross-linkages occur sufficiently at this degree of admixture.

From the glass transition temperature Tg in FIGS. 1 and 2, it is further to be understood that the glass transition temperature Tg gradually decreases as the proportion of the epoxy resin curing agent (B) is increased.

TABLE 1

|  | IZOD (kg·g/cm$^2$) | Tg (°C.) | Bending Strength (kg/mm$^2$) | Bending Modulus of Elasticity (kg/mm$^2$) | CAI (kg/mm$^2$) 1500 in-lb/in |
| --- | --- | --- | --- | --- | --- |
| Ref. Ex. 1 | 7.0 | 205 | 15.6 | 392 | 35 |
| Ex. 1 | 9.0 | 216 | 15.6 | 390 | 37 |
| Ex. 2 | 9.5 | 221 | 15.5 | 395 | 38 |
| Ex. 3 | 9.1 | 223 | 15.8 | 408 | 38 |
| Ex. 19 | 3.2 | 224 | 15.5 | 405 | 25 |
| Comp. Ex. 1 | 1.4 | 225 | 15.8 | 410 | 10 |
| Ref. Ex. 2 | 11.2 | 135 | 13.2 | 318 | 42 |
| Ex. 4 | 12.8 | 139 | 13.1 | 333 | 44 |
| Ex. 5 | 13.2 | 143 | 13.7 | 330 | 45 |
| Ex. 6 | 13.0 | 147 | 13.5 | 331 | 43 |
| Ex. 20 | 3.8 | 148 | 13.5 | 330 | 26 |
| Comp. Ex. 2 | 1.5 | 148 | 13.5 | 332 | 13 |
| Ex. 7 | 7.2 | 181 | 13.7 | 333 | 37 |
| Ex. 8 | 14.5 | 130 | 13.5 | 330 | 48 |
| Ex. 9 | 6.8 | 185 | 13.0 | 365 | 37 |
| Ex. 10 | 10.5 | 130 | 13.2 | 304 | 40 |
| Ex. 11 | 8.8 | 156 | 14.8 | 360 | 35 |
| Ex. 12 | 9.0 | 170 | 15.1 | 375 | 39 |
| Ex. 13 | 8.2 | 185 | 15.2 | 386 | 40 |
| Ex. 14 | 11.0 | 130 | 13.5 | 314 | 43 |
| Ex. 15 | 7.5 | 168 | 14.5 | 408 | 38 |
| Ex. 16 | 8.9 | 215 | 14.8 | 375 | 38 |
| Ex. 17 | 9.2 | 218 | 15.0 | 388 | 36 |
| Ex. 18 | 14.0 | 130 | 13.3 | 328 | 46 |
| Comp. Ex. 3 | 2.6 | 126 | 13.6 | 330 | 18 |
| Comp. Ex. 4 | 1.8 | 145 | 12.8 | 281 | 16 |
| Comp. Ex. 5 | 1.3 | 210 | 15.5 | 402 | 8 |

We claim:

1. A curing agent composition consisting essentially of a first curing agent which is capable of cross-linking an epoxy resin and which is at least one member selected from the group consisting of aliphatic primary amines, polyamido primary amines, dicyanopolyamides, bisphenols, phenolic resins, vinylphenol polymers and acid anhydrides, and a second curing agent which is at least one compound represented by the following general formula:

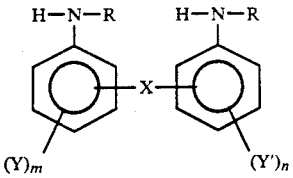

wherein X is —CR$_1$R$_2$—, —CO—, —COO—, —SO$_2$—, —SO—, —S—, —O—, —NR$_1$—, —Sir$_1$R$_2$— or —POR$_1$— where R$_1$ and R$_2$ each stands for hydrogen, a lower alkyl or a phenyl; Y and Y' each stands for hydrogen, a lower alkyl or an electron attracting group; R is a lower alkyl; and m and n each is an integer of 1–4.

2. A curing agent composition as set forth in claim 1, wherein said first and second curing agents are used in amounts so that said first and second curing agents account for 85 to 5% and 15 to 95%, respectively, of a total of the amounts of active hydrogen of said first and second curing agents.

3. A curing agent composition as set forth in claim 1, wherein said first curing agent is at least one acid anhydride selected from the group consisting of maleic anhydride, succinic anhydride, methyltetrahydrophthalic anhydride, methylnadic anhydride and methylhexahydrophthalic anhydride.

4. A curing agent composition as set forth in claim 1, wherein said first curing agent is dicyanodiamide or methylhexahydrophthalic anhydride.

5. A curing agent composition as set forth in claim 1, wherein R is an alkyl having 1–3 carbon atoms, X is —CH$_2$—, —SO$_2$—, —CO—, —O—, —C(CH$_3$)$_2$—, —CHC$_6$H$_5$—, or —CR$_1$R$_2$— Y and Y' each is hydrogen, a lower alkyl, a halogen, a nitro group or trifluoromethyl, R$_1$ and R$_2$ each is an alkyl having 1–3 carbon atoms, and m and n each is 1 or 2.

6. A curing agent composition as set forth in claim 1 wherein X is —CO—, —COO—, —SO$_2$—, —SO—, —S—, —O—, —NR$_1$—, —SiR$_1$R$_2$— or —POR$_1$— where R$_1$ and R$_2$ each stands for hydrogen, a lower alkyl or a phenyl.

* * * * *